United States Patent
Holt

(10) Patent No.: US 9,052,265 B2
(45) Date of Patent: Jun. 9, 2015

(54) METHOD AND APPARATUS TO FACILITATE DETERMINATION OF A PARAMETER THAT CORRESPONDS TO A SCANNING GEOMETRY CHARACTERISTIC

(75) Inventor: Kevin Holt, Chicago, IL (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1287 days.

(21) Appl. No.: 11/419,793

(22) Filed: May 23, 2006

(65) Prior Publication Data

US 2007/0274456 A1 Nov. 29, 2007

(51) Int. Cl.
G01N 23/04 (2006.01)
A61B 6/03 (2006.01)
A61B 6/00 (2006.01)

(52) U.S. Cl.
CPC .............. *G01N 23/046* (2013.01); *A61B 6/032* (2013.01); *A61B 6/583* (2013.01); *G01N 2223/419* (2013.01)

(58) Field of Classification Search
CPC ... G01D 18/00; G01D 5/24452; A61B 6/583; A61B 2017/00712; A61B 6/582; G21K 1/025; G21K 5/04; G21K 5/10; G01T 7/005
USPC ...................... 378/4, 205, 210, 901, 128–131
See application file for complete search history.

(56) References Cited

U.S. PATENT DOCUMENTS

| | | | | |
|---|---|---|---|---|
| 5,390,112 | A * | 2/1995 | Tam ................................ | 378/17 |
| 2005/0041771 | A1 * | 2/2005 | Kuo-Petravic et al. ......... | 378/19 |
| 2005/0276375 | A1 * | 12/2005 | Urushiya ........................ | 378/19 |

FOREIGN PATENT DOCUMENTS

| | | | | |
|---|---|---|---|---|
| JP | | 2004037267 A | * | 2/2004 |
| JP | | 2004061256 A | * | 2/2004 |
| WO | WO 2007043974 A1 | | * | 4/2007 |

OTHER PUBLICATIONS

Crawford et al., Reconstruction for fan beam with an angular-dependent displaced center-of-rotation, 1998, Medical Physics, vol. 15, No. 1, pp. 67-71.*
Concepcion et al., CT Fan Beam Reconstruction with a Nonstationary Axis of Rotation, Mar. 1992, IEEE Transactions on Medical Imaging, vol. 11, No. 1, pp. 111-116.*
Song et al., Development and Evaluation of a MicroCT System for Small Animal Imaging, Nov. 2001, IEEE 2001 Nuclear Science Conference Record, vol. 3, pp. 1600-1604.*

(Continued)

*Primary Examiner* — David J Makiya
*Assistant Examiner* — John Corbett
(74) *Attorney, Agent, or Firm* — Fitch, Even, Tabin & Flannery LLP

(57) ABSTRACT

Relative movement about an axis of rotation is caused as between an energy source/detector array with respect to an object (where the object can comprise either an object to be projected to facilitate a study of the object or a calibration object to be projected as part of calibrating usage of the energy source/detector array). The energy source/detector array are used during this relative movement to scan the object and to obtain corresponding object project data. That object projection data is then used to determine a parameter as corresponds to at least one scanning geometry characteristic as corresponds to using the energy source and the corresponding detector array while causing the aforementioned relative movement to scan the object.

15 Claims, 3 Drawing Sheets

(56) References Cited

OTHER PUBLICATIONS

Gullberg et al., Estimation of Geometrical parameters for fan beam tomography, 1987, Physics in Medicine and Biology, vol. 32, No. 12, pp. 1581-1594.*
Bushberg et al., The Essential Physics of Medical Imaging, 2002, ISBN 0-683-30118-7.*
X-ray or Gamma Ray Systems or Devices, USPTO Class Definitions.*
PTO 10-5396, English Translation for JP2004061256A.*
Press et al., Numerical Recipes in C, 2002, ISBN 0-521-43108-5, pp. 397-402.*
PTO 10-5395, English Translation for JP2004-37267A.*
Holt, Geometric Calibration and Distortion Calibration for CT from Scans of Unknown Objects Using Complementary Rays, 2009, SPIE, vol. 7258, pp. 1Q-1 to 1Q-11.*
Holt, Geometric Calibration of Third-generation Computed Tomography Scanners from Scans of Unknown Objects using Complementary Rays, 2007, IEEE, ICIP 2007, pp. IV-129 to IV-132.*
Silver, Michael D., Specification for wACTIS PreProcessing, Bio-Imaging Research, Inc., 39 pages, Revision R4.12 Aug. 11, 2006.
Press, William H.; Teukolsky, Saul A.; Vetterling, William T.; and Flannery, Brian P., Numerical Recipes in C, The Art of Scientific Computing, Copyright © Cambridge University Press 1988-1992, Australia, cover page-p. xv (13 pages), Printed with corrections 2002.
Press, William H.; Teukolsky, Saul A.; Vetterling, William T.; and Flannery, Brian P., Numerical Recipes in C, The Art of Scientific Computing, Chapter 10. Minimization or Maximization of Functions; Copyright © Cambridge University Press 1988-1992, Australia, 62 pages, Printed with corrections 2002.
Press, William H.; Teukolsky, Saul A.; Vetterling, William T.; and Flannery, Brian P., Numerical Recipes in C, The Art of Scientific Computing, Chapter 15.4 General Linear Least Squares, Copyright © Cambridge University Press 1988-1992, Australia, 11 pages, Printed with corrections 2002.
Silver, Michael D., Specification for wACTIS CRAY, Bio-Imaging Research, Inc., 17 pages, Revision 1.5 May 23, 2005.
Zamyatin, Alexander A.; Taguchi, Katsuyuki; and Silver, Michael D., Helical Cone Beam CT with an Asymmetrical Detector, Medical Physics, vol. 32, No. 10, Oct. 2005, pp. 3117-3127.
Silver, Michael D., Specification for wACTIS Backprojection, Bio-Imaging Research, Inc., 30 pages, Revision R4.4 Sep. 15, 2005.
Drawing Sheet—wACTIS Master Geometry Document, Jan. 23, 2004, 1 page.

* cited by examiner

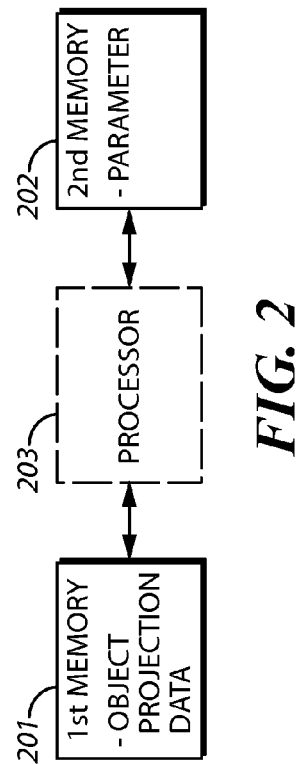
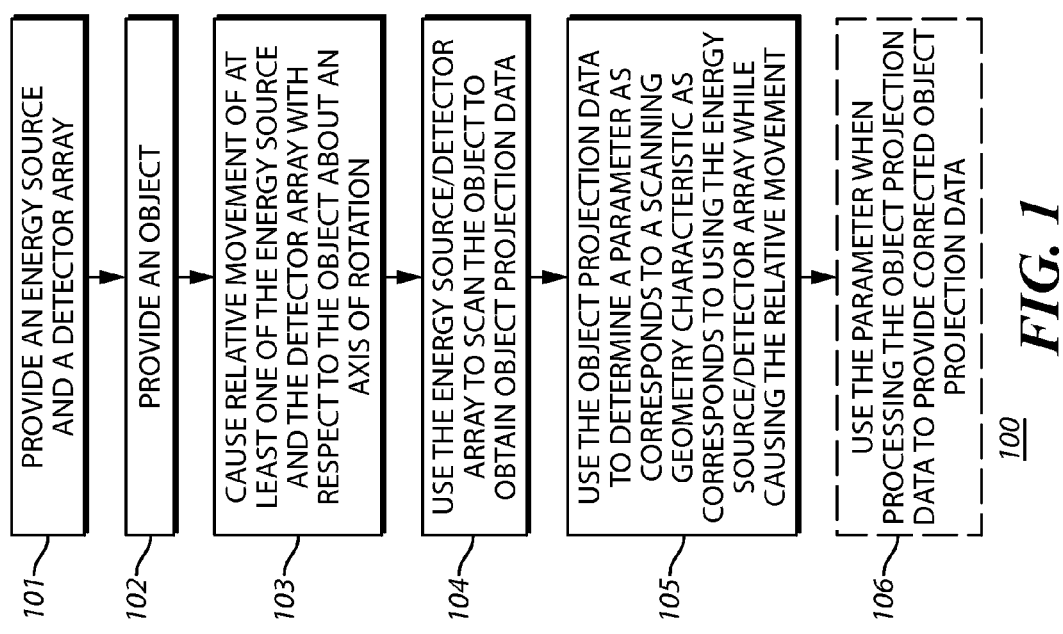

US 9,052,265 B2

METHOD AND APPARATUS TO FACILITATE DETERMINATION OF A PARAMETER THAT CORRESPONDS TO A SCANNING GEOMETRY CHARACTERISTIC

TECHNICAL FIELD

This invention relates generally to computed tomography.

BACKGROUND

Computed tomography is known in the art. By one approach, sometimes referred to as third generation computed tomography, a fan beam or a cone beam facilitates the gathering of object data while the object being scanned and the X-ray source/detector rotate with respect to one another. In general, these approaches entail the capture and processing of data as corresponds to a relatively large number of rotationally differentiated views.

In practice, a number of practical limitations can make it difficult to properly interpret such data. As one example, a given detector array may be comprised of a plurality of discrete elements that are not necessarily all exactly equally spaced apart. As another example, and particularly when using curved detector arrays, focus issues can become problematic. Therefore, for these and other reasons, it may be useful and/or necessary to calibrate a given X-ray source/detector platform from time to time to attempt to minimize such problems.

Such calibration, however, can present unwanted issues in and of itself. A calibration exercise typically represents downtime for the platform; that is, the platform cannot be used for real tasks while being calibrated. Furthermore, in at least some cases, calibration does not necessarily assure that the platform is now assured of providing useful results. For example, calibration usually entails use of a calibration object (such as a metal pin). The form factor and weight of this calibration object will often differ from that of a real object of interest. This, in turn, can lead to different interactions between the real object of interest and the platform than as are experienced by the calibration object (for example, a rotating turntable may tilt slightly when supporting a large real object of interest as compared to when supporting a calibration object). In other cases, the pin itself may be quite tall (when calibrating, for example, a tall scanning apparatus). In such a case, centrifugal force can cause considerable wobbling of the pin. Such undesired movement, of course, can also impact calibration accuracy and/or calibration time requirements.

The prior art, then, presents a troubling conundrum. Scanning results can be unreliable or at least less useful in the absence of calibration. At the same time, calibration itself is often viewed as an unproductive activity to be avoided if possible, and one that may not lead in any event to a reliably conducted scanning process.

BRIEF DESCRIPTION OF THE DRAWINGS

The above needs are at least partially met through provision of the method and apparatus to facilitate determination of a parameter that corresponds to a scanning geometry characteristic described in the following detailed description, particularly when studied in conjunction with the drawings, wherein:

FIG. 1 comprises a flow diagram as configured in accordance with various embodiments of the invention;

FIG. 2 comprises a block diagram as configured in accordance with various embodiments of the invention;

Figure 3:
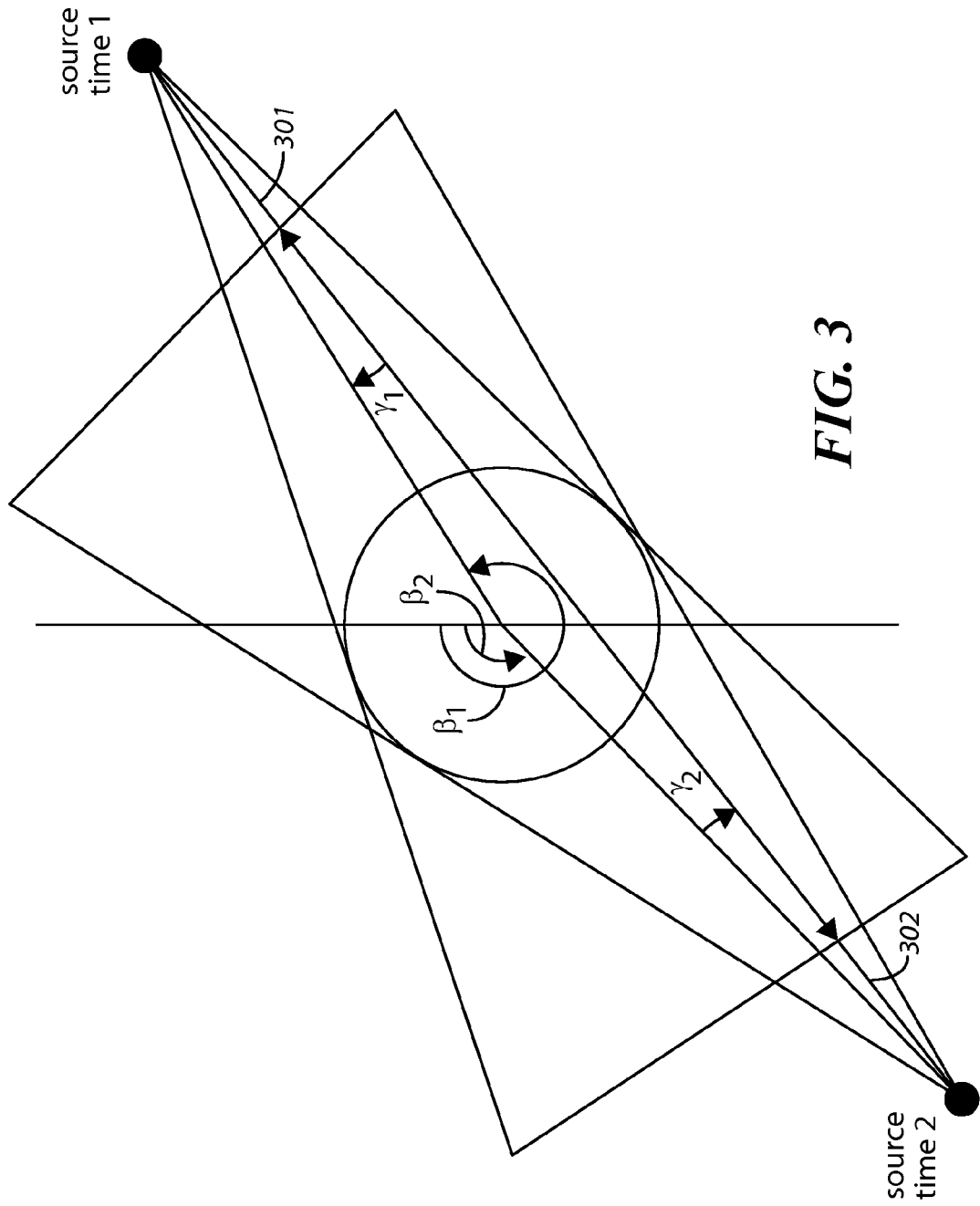
FIG. 3 comprises a top plan schematic view as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary meaning as is accorded to such terms and expressions with respect to their corresponding respective areas of inquiry and study except where specific meanings have otherwise been set forth herein.

DETAILED DESCRIPTION

Generally speaking, pursuant to these various embodiments, relative movement about an axis of rotation is caused as between an energy source/detector array with respect to an object (where the object can comprise either an object to be projected to facilitate a study of the object or a calibration object to be projected as part of calibrating usage of the energy source/detector array). The energy source/detector array are used during this relative movement to scan the object and to obtain corresponding object projection data. That object projection data is then used to determine a parameter as corresponds to at least one scanning geometry characteristic as corresponds to using the energy source and the corresponding detector array while causing the aforementioned relative movement to scan the object.

By one approach this scanning geometry characteristic can comprise, for example, a value that corresponds to a location of the axis of rotation, a value that corresponds to sample pitch, or the like. By one approach, this determination can comprise processing the object projection data to provide a first set of projection data formed using a set of data points, then using a selected value for the parameter and data comprising complements to the first set of data points to provide a second set of projection data, and comparing the first set of projection data to the second set of projection data to determine a measure of similarity.

By one approach, when this measure of similarity comprises an acceptable measure of similarity, the corresponding selected value for the parameter is then used to describe the scanning geometry characteristic of interest. When such is not the case, these teachings further accommodate selecting a new different value for the parameter and using the new value for the parameter while repeating the above recited steps.

So configured, these teachings permit considerable improvement with respect to processing projection data while essentially avoiding, if desired, a specific calibration step. While it is quite possible to employ these practices with a calibration object if desired, this is not necessary as these teachings permit, in effect, a kind of on-the-fly calibration that permits both the scanning of an object of interest and a corresponding adjustment of the resultant data to compensate for physical anomalies and circumstances that would otherwise lead to distortions in that resultant data. This can comprise, for example, identification of a central ray or other geometrical parameters of interest (such as, for example, the fan angle).

These and other benefits may become clearer upon making a thorough review and study of the following detailed description. Referring now to the drawings, and in particular to FIG. 1, an illustrative process 100 includes the provision 101 of an energy source (such as an X-ray energy source) and a corresponding detector array. Such sources and detector arrays are known in the art and require no further elaboration here.

This process 100 also provides 102 an object. This object may comprise either an object to be projected to facilitate a study of the object (i.e., an object of interest) or may comprise a calibration object to be projected as part of calibrating usage of the energy source and the corresponding detector array. These teachings are generally applicable in either case. In many cases, of course, it will likely be preferred to eschew the use of a calibration object and to facilitate these teachings with an object of interest instead. (Those skilled in the art will recognize and understand that the terms projected and projection refer to any of a variety of scanned data deliverables including but not limited to representational two and three-dimensional data sets (where each datum in a projection essentially summarize the total amount of material traversed along a single ray path).

This process 100 then causes 103 relative movement of at least one of the energy source and the corresponding detector array with respect to the object about an axis of rotation. Those skilled in the art will understand that there are various ways to accomplish such rotational relative movement. For example, by one approach, the object can be held or otherwise supported (using a corresponding support structure such as a table surface or a jig or other gripping mechanism of choice) with the support structure (and hence the object) then rotating about the axis of rotation (those skilled in the art often refer to such an approach as comprising third generation industrial geometry). By another approach, the object remains relatively stationary while both the energy source and the detector array rotate about the axis of rotation (those skilled in the art often refer to such an approach as comprising third generation medical geometry). By yet another approach, the object remains relatively stationary while the energy source rotates about the axis of rotation (those skilled in the art often refer to such an approach as comprising fourth generation geometry). If desired, such relative motion can be achieved by rotating both the object and the source/detectors, though such a configuration will likely entail increased complexity.

This process 100 then provides for using 104 the energy source and the corresponding detector array while causing such relative movement to scan the object to thereby obtain corresponding object projection data. Again, such actions are well understood in the art and require no further elaboration here.

This process 100 then provides for using 105 that object projection data to determine a parameter that corresponds to at least one scanning geometry characteristic as corresponds in turn to using the energy source/detector array while causing the aforementioned relative movement to scan the object. This can comprise, for example, using the object projection data which has been preprocessed using any number of processing steps known in the art, including but not limited to linear filtering, median filtering, detector resampling, view resampling, logarithmic conversion, and corrections for electronic offset, electronic gain, electronic nonlinearity, source falloff, source fluctuations, beam hardening, low photon counts, rings, crosstalk, and temporal lag. The specific scanning geometry characteristic can vary with the needs and/or opportunities presented by a given application context. Examples, however, would include a value that corresponds to a location of the axis of rotation, a value that corresponds to sample pitch, and so forth. (More specific illustrative examples in this regard are provided further below.)

By one approach, this determination can comprise processing the object projection data to provide a first set of projection data that is formed using a set of data points. One then uses a selected value for the parameter and data comprising complements to the set of data points to thereby provide a second set of projection data. There are various ways by which this selected value can be chosen. By one approach, for example, the selected value is chosen from amongst a plurality of provided candidate parameter values (for example, three, five, a hundred, or even a thousand or more different candidate parameter values can be provisioned for this purpose).

A comparison between the first set of projection data and the second set of projection data then yields a useful measure of similarity. There are various ways by which this comparison may be accomplished. By one approach, this can comprise determining a distance (such as, but not limited to, a mean squared error) as corresponds to differences between the first set of projection data and the second set of projection data. By another approach, this can comprise determining information (such as, but not limited to, mutual information) between the first set of projection data and the second set of projection data. By yet another approach, this can comprise determining a correlation (such as, but not limited to, a cross correlation) between the first set of projection data and the second set of projection data. Other possible approaches may be available as well depending upon the application context.

The above described approach basically serves to form an entire first set of projection data and then to form an entire second set of projection data. A similarity measure between the two full sets is then found followed by throwing away the formed projection data (or at least the second set of projection data). An alternative approach would comprise proceeding on a datum-by-datum basis. For the first datum in the first set, one can calculate the corresponding datum in the second set, then calculate the contribution of that pair of data to the similarity measure and record that result into a running tally, and then throw away that datum and move on to the next. Both such approaches offer their respective strengths and tradeoffs with one or the other likely being a somewhat better choice as a function of the specifics of a given application setting.

By one approach, one may then determine whether this measure of similarity comprises an acceptable measure of similarity. This can comprise, for example, taking into account previous selections and comparisons as pertain to this parameter to determine whether the present result is acceptable at least from a relative standpoint.

When this measure of similarity does comprise an acceptable measure of similarity, the selected value for the parameter can then be used, for example, to describe the scanning geometry characteristic of interest. This parameter may then be used as desired. By one approach, this process 100 will accommodate using this parameter when processing the object projection data to provide a reconstructed image of the scanned object. By another approach, this process 100 will accommodate using 106 this parameter when processing the object projection data to provide corrected object projection data. By another approach, one can utilize this parameter when realigning the system to obtain a desired geometry setup.

When this measure of similarity does not comprise an acceptable measure of similarity, one may select a new value for the parameter (which new parameter is different than the previously selected value for the parameter) and then use that new value as the selected value for the parameter while repeating the above steps beginning with using a selected value for the parameter and processing the object projection data. By one approach, selecting a new value can comprise deletion of a previously selected candidate parameter value and then adding a new candidate parameter value to the plurality of candidate parameter values to thereby provide a new plurality or pool of candidate parameter values. A new value may then be selected from amongst this new plurality of candidate parameter values.

In general, at some point, this iterative process should identify a parameter value that ultimately corresponds to an acceptable measure of similarity.

Those skilled in the art will appreciate that the above-described processes are readily enabled using any of a wide variety of available and/or readily configured platforms, including partially or wholly programmable platforms as are known in the art or dedicated purpose platforms as may be desired for some applications. Referring now to FIG. 2, an illustrative approach to such a platform will now be provided.

By one approach this apparatus can comprise a first memory 201 and a second memory 202. These memories 201 and 202, in turn, can optionally operably couple to a processor 203 of choice. The first memory 201 can store, for example, the aforementioned objection projection data while the second memory 202 can store, for example, the aforementioned parameter. The processor 203, in turn, can be configured and arranged, via, for example, appropriate programming, to effect the above-described teachings. This can include, of course, using the object projection data to iteratively determine a parameter that corresponds to a scanning geometry characteristic of interest and choice.

Those skilled in the art will recognize and understand that such an apparatus may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

More specific examples will now be provided. Those skilled in the art will understand and recognize that these examples are provided for the sake of illustration rather than limitation and that the points of specificity provided are not intended as an exhaustive presentation.

Many of the keywords and variables as appear in the following examples are defined as follows (note also that C-language indexing is used (starting from 0) and all angles are expressed in radians):

equi-angular—detector channels are spaced at equal angles (i.e. curved detector)

equi-spatial—detector channels are spaced at equal distances along a straight line (i.e. flat detector)

complementary rays—two rays which occupy the same ray path from opposite directions complementary sinogram—a sinogram made by replacing the value of every ray with its complement MSE—mean square error between a sinogram and its complement search window—range of values in which the search algorithm is allowed to look bracket—current list of three points used in the search algorithm Notation:
P(channel,view,z)—logged, preprocessed acquired data (known as projection data)
Q(channel,view,z)—complementary sinogram
Channel—channel number
View—view number
Z—slice position number
$N_{channels}$—number of channels in the detector
$N_{views}$—number of rotational positions in one scan
$\gamma$—angle of a source ray relative to central ray
$\beta$—rotation position angle
$\Delta\beta$—rotation increment
dir—rotation direction
detPitch—physical detector pitch at the detector (mm)
SID—source-to-detector distance during the original acquisition (mm)
$c_{ray}$—central ray: index of the ray from the source through the rotation axis
$\Delta\gamma$—angular sample spacing at isocenter
FA—full fan-angle Search Inputs:
InterpKernelWidth—width of interpolation kernel
CSearchMin,CsearchMax—central-ray search window
FSearchMin,FsearchMax—sample-spacing search window
Cres—central ray search resolution
Fres—sample spacing search resolution
cmpchmin, cmpchmax—range of channels to compare complementary rays
scanmin, scanmax—range of scans or slices to compare complementary rays
MinOverlap—minimum number of redundant channels required by search
MaxIters—maximum number of iterations allowed in search algorithm
$\alpha_C, \alpha_F$—bracket widening factors Intermediate values:
cha, chb—range of channels which contain redundant rays
c(1),c(1),c(2)—central ray search bracket
f(0),f(1),f(2)—sample spacing search bracket
e( . . . )—error evaluated at bracket points In general, for many rays emitted by the energy source, there is another ray from another view that occupies the same ray path. Two such rays are called complementary. For a given ray, the view position and channel position of the complementary ray are found as functions of a central ray value and of the sample spacing. The algorithms in this particular embodiment work by searching for the central ray (and optionally the sample spacing) values that minimize the average discrepancy between the original rays and their complements.

FIG. 3 illustrates the concept of complementary rays. At time 1 for some ray 301 with channel angle $\gamma_1$ when the table is at position $\beta_1$, there is another ray 302 specified at time 2 by ($\gamma_2,\beta_2$) that occupies the same path. Ideally, the detector readings for these two rays should be identical or at least very similar. The correspondence between a ray and its complement is:

$$\gamma_2 = -\gamma_1 \qquad (1)$$

$$\beta_2 = \beta_1 + \pi + 2\times\gamma_1 + 2\pi k \qquad (2)$$

where k is any integer. In general the mapping between a channel number and γ depends on both the central ray and the sample spacing. Conversely, differences in these detector readings for these two rays correspond to errors when processing the object projection data in an uncalibrated manner.

These illustrative embodiments can be applied in either of two ways; via a standard calibration approach or as an on-the-fly calibration exercise.

A standard calibration approach may comprise performing two scans: a calibration scan and then a normal object scan for reconstruction. The process 100 runs on the data obtained from the first of these two scans. If desired, the geometry information can be calculated for every slice position or for just a few sparse slice positions. The procedure for standard calibration as per these teachings is essentially the same as a normal calibration method except that an arbitrary object may be used instead of a pin.

For on-the-fly calibration, this algorithm may be applied to object-scan data as the first step in reconstruction. No separate calibration scan is necessary using either the object of interest or a specific calibration object. This holds true notwithstanding that the exact geometry is unknown prior to reconstruction.

For both standard and on-the-fly calibration, preprocessing may proceed generally the same as for a normal object scan, including linear filtering, median filtering, detector resampling, view resampling, logarithmic conversion, and/or corrections for electronic offset, electronic gain, electronic non-linearity, source falloff, source fluctuations, beam hardening, low photon counts, rings, crosstalk, and/or temporal lag.

The object to be used for the scan in accordance with these teachings may be any object (but there should be an object present and not merely air). For standard calibration, this may be the same object that will be scanned for reconstruction, or it can be different. For example, the algorithm may be applied to a conventional pin calibration scan in order to find central ray. Using the algorithm to find sample spacing will likely have improved results if the scan object occupies a large portion of the FOV. For on-the-fly calibration, the object (and data) is the same as what will be reconstructed.

Figure 4:
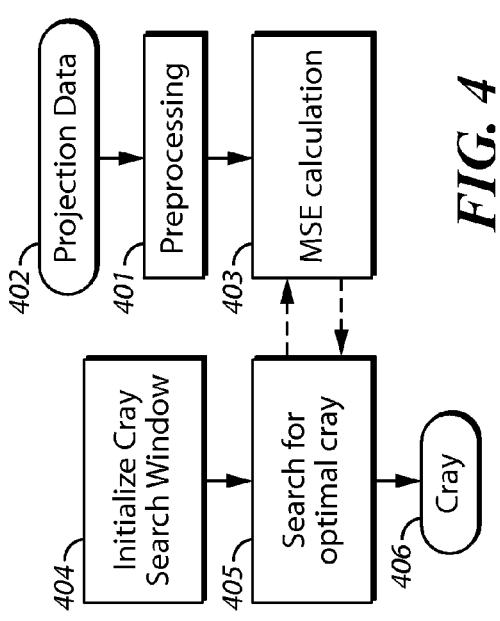
FIG. 4 comprises a flow diagram as configured in accordance with various embodiments of the invention.
Figure 5:
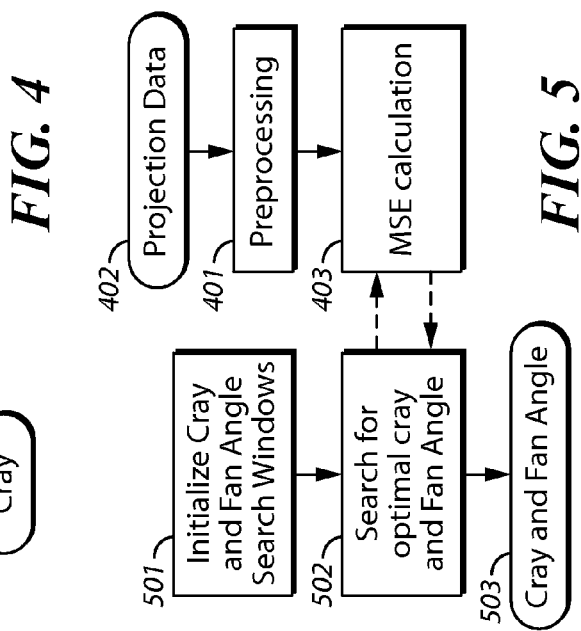
FIG. 5 comprises a flow diagram as configured in accordance with various embodiments of the invention.

The basic algorithms for each mode are illustrated in FIG. 4 (which illustrates a Cray-only approach) and FIG. 5 (which illustrates a Cray plus sample-spacing approach). The algorithms can be the same whether used for standard calibration or on-the-fly calibration. Both approaches shown here operate by preprocessing 401 the available object projection data 402 (which can comprise, by one approach, taking log values or log-like values of the available object projection data 402) and making calculations 403 to search for the minimum value of a mean-square-error (MSE) measurement between a sinogram and its complement. These algorithms repeatedly make different guesses regarding the central ray 404 (and optionally the sample spacing as well 501) and then search for an optimal cray result 405 (and optionally an optimal sample spacing result 502 as well) by evaluating the MSE for each guess and then refine the guess to arrive iteratively at a final result 406, 503.

Figure 6:
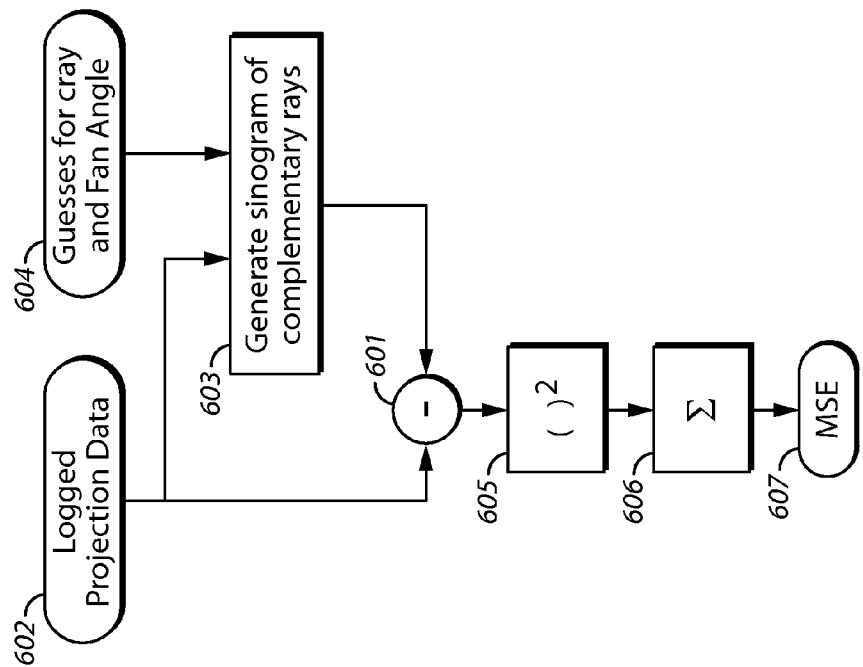
FIG. 6 comprises a flow diagram as configured in accordance with various embodiments of the invention.

FIG. 6 generally depicts one illustrative approach towards effecting the above-described MSE calculation. Viewed generally, this approach provides for comparing logged object projection data 602 with data comprising a sinogram of complementary rays 603 as generated using the logged projection data 602 and initial (or subsequently changed) cray (and optionally sample spacing) value guesses 604. The comparison results are squared 605 and summed 606 to yield a mean squared error 607.

The following definitions are pertinent to a more detailed discussion in this regard that follows:

Input:

P(channel,view,scan)—Logged input projection data scanmin, scanmax—Range of scan indices to use in calculation cmpchmin, cmpchmax—Range of channels for which to compare complementary rays MinOverlap—Minimum required number of redundant channels ViewsPer360—Number of views per 360 degree revolution Rotdir—rotation direction (1==beta increases with view, −1==beta decreases)

InterpKernelWidth—width of channel-interpolation kernel

Function Parameters:

c—Intermediate guess for central ray (provided by algorithm)

Δγ—Guess for sample angular spacing (provided as input or by algorithm)

Intermediary:

Q(channel',view',scan)—Complementary projection data

Ouput:

MSE(c,Δγ)—Mean-square error between sinogram and the compliment

This algorithm allows multiple scans to be used to compute a single central ray. This, in turn, contributes to better noise immunity. The multiple scans may be multiple rotations at the same slice position, or they may be rotations at sequential slice positions. The first approach might be used for standard calibration, whereas the second may be useful for either standard calibration or on-the-fly calibration.

For a sinogram image P(channel,view,scan) and some values of c and Δγ, one may calculate the complementary sinogram, Q, for the same scan as follows:

$$Q_{c,\Delta\gamma}(\text{channel}',\text{view}',\text{scan}) = \text{Interploate}(P; \text{channel}, \text{view},\text{scan}) \quad (3)$$

where P is interpolated to the fractional coordinates described by:

$$\text{channel} = 2c - \text{channel}' \quad (4)$$

and, for an equi-angular array:

$$\text{view} = \text{view}' + \frac{\text{ViewsPer}360}{2} + 2(\text{channel}' - c)\frac{\Delta\gamma}{\Delta\beta} \quad (5)$$

and for an equi-spatial array:

$$\text{view} = \text{view}' + \frac{\text{ViewsPer}360}{2} + 2\frac{\tan^{-1}((\text{channel}' - c)\Delta\gamma)}{\Delta\beta} \quad (6)$$

Those skilled in the art will recognize that equations 4, 5, and 6 can be readily generalized to incorporate additional geometric parameters, and to handle alternate geometries, including but not limited to polygonal arrays, irregularly spaced arrays, and irregularly spaced views.

Views are preferably equally spaced by rotational increment $\Delta\beta$, $$\Delta\beta = dir \times \frac{2\pi}{ViewsPer360}$$

In general, channel and view will be fractional, so one may use interpolation. Additionally, the view may need to wrap around 360°. Thus, equation 3 may be performed as follows:

$$view_a = \text{floor}(posfmod(view, ViewsPer360)) \quad (7)$$

$$view_b = \text{floor}(posfmod(view+1, ViewsPer360)) \quad (8)$$

where
ViewsPer360 is the number of views in a 360° acquisition (this can be fractional); and
posfmod is the floating-point positive modulus, defined as $$posfmod(x, y) = x - y \times \text{floor}\left(\frac{x}{y}\right)$$

To efficiently perform channel-interpolation, one may first pre-calculate a set of interpolation weights. This step is done once for each central-ray guess:

1. Calculate partial-shift amount $$\text{shift} = 2 \times cray - \text{floor}(2 \times cray) \quad (9)$$

2. Calculate a truncated sinc function with an applied Hanning window $$s_k = \begin{cases} 1, & |\text{shift}-k| = 0 \\ \frac{\sin(\pi(\text{shift}-k))}{\pi(\text{shift}-k)} \times \frac{1+\cos\left(\frac{\pi(\text{shift}-k)}{InterpKernelWidth}\right)}{2}, & 0 < |\text{shift}-k| \le InterpKernelWidth \\ 0, & |\text{shift}-k| > InterpKernelWidth \end{cases} \quad (10)$$

3. Normalize the truncated sinc function $$h_k = \frac{s_k}{\left(\sum_{k=-InterpKernelWidth}^{InterpKernelWidth-1} s_k\right)} \quad (11)$$

where steps 2 and 3 are performed for all k in the range −InterpKernelWidth≤k≤(InterpKernelWidth+1). Performance will tend to be best when InterpKernelWidth is an even number, and it should generally be at least 6. A value of 10 is recommended. In general, the larger the value, the longer the processing time but the better the noise immunity.

Channel interpolation is then performed according to:

$$a = \sum_{k=-InterpKernelWidth}^{InterpKernelWidth+1} P(\text{floor}(channel) + k, view_a, scan) \times h_k \quad (12)$$

$$b = \sum_{k=-InterpKernelWidth}^{InterpKernelWidth+1} P(\text{floor}(channel) + k, view_b, scan) \times h_k \quad (13)$$

And view-interpolation is then used to make the complementary sinogram:

$$w = posfmod(view, ViewsPer360) - view_a \quad (14)$$

$$Q_{cray, \Delta\gamma}(channel', view, scan) = a + w \times (b-a) \quad (15)$$

Note that Q is a function of cray, $\Delta\gamma$, and $\Delta\beta$.

Alternatively, one could just use bilinear interpolation by skipping equations 9-11 and replacing equations 12 and 13 with:

$$a = P(\text{floor}(channel), view_a, scan) + (channel - \text{floor}(channel)) \times [P(\text{ceil}(channel), view_a, scan) - P(\text{floor}(channel), view_a, scan)] \quad (16)$$

$$b = P(\text{floor}(channel), view_b, scan) + (channel - \text{floor}(channel)) \times [P(\text{ceil}(channel), view_b, scan) - P(\text{floor}(channel), view_b, scan)] \quad (17)$$

In general, bilinear interpolation (equations 16 and 17) allows the algorithm to run much faster than with truncated sinc interpolation (equations 12 and 13). However, when the data contains a lot of noise, truncated sinc interpolation (equations 12 and 13) can cause the algorithm to be significantly more stabile and accurate than with bilinear interpolation (equations 16 and 17). When the data contains little noise, there is generally little stability difference between the two methods, so bilinear interpolation may be preferred for its faster speed.

In equation 15, boundary conditions should be treated as follows. For channel<0 or channel>(Nch−1), replicate the end channel. For values where $view_a$>(Nviews−1) or $view_b$>(Nviews−1), set Q=0 (this should only happen for <360° scans) (note that $view_a$<0 or $view_b$<0 should never occur).

The MSE calculation is as follows:

$$MSE(cray, \Delta\gamma) = \frac{1}{Npix} \sum_{scan=scanmin}^{scanmax} \sum_{view=0}^{Nviews-1} \sum_{channel'=cha}^{chb} \quad (18)$$

$$(P(channel', view, scan) - Q_{cray, \Delta\gamma}(channel', view, scan))^2$$

where $$cha = \max(chcmpmin, \text{ceil}(2 \times c) - (Nch - 1)) \quad (19)$$

$$chb = \min(chcmpmax, \text{floor}(2 \times c)) \quad (20)$$

$$Npix = Nviews \times (chb - cha + 1) \times (scanmax - scanmin + 1) \quad (21)$$

If chb<(cha+MinOverlap) then an error condition or warning can be returned as follows:
insufficient redundant data.

The parameters chcmpmin and chcmpmax may be used to save computation and avoid possible complications from edge channels. For best performance for nontruncated scans, this range should be set to cover slightly more than the full span of the object in P. For truncated or asymmetric configurations, for best results one should determine a range of channels for which complementary rays are expected to exist, then set chcmpmin and chcmpmax to be slightly within this range.

When in doubt, however, one may generally use:
cmpchmin=0
cmpchmax=Nch−1
Note that Q only actually needs to be calculated for channels cha to chb. Additionally, Q need not be computed in its entirety—for each value inside the sum (18), one can just calculate the appropriate value of equation 15. This makes efficient use of memory since one need not ever store the entire Q array.

As noted, one may employ these teachings while searching only for the central ray. To calculate the central ray, one finds the value that minimizes MSE(cray,$\Delta\gamma$). Here, $\Delta\gamma$ is the value returned from an alternate calibration method known in the art, or it may be the value returned from the calibration algorithm run in central-ray-and-sample-spacing mode if that mode was previously run, or it may be set equal to the nominal value of:

$$\Delta\gamma_o = \frac{detPitch}{SID} \quad (22)$$

Finding the minimum of MSE is a non-trivial problem, as searching for the minimum value can require many evaluations of MSE, each of which may be computationally costly.

To find the minimum, one could use a brute force search, which is slow but can guarantee success. For well conditioned searches like central ray, iterative search algorithms can run much quicker than the brute force method, as well as return more accurate answers. One can use off-the-shelf iterative algorithms, such as "Golden Section Search" or "Brent's Method." In the alternative, a new algorithm is presented here. When initialized properly, all such search algorithms are equivalent and will return the same central ray value to within some small user-specified tolerance. The algorithms, however, differ in their convergence speed and in how they respond to poor initializations. Consider the method presented below.

Inputs:
SearchMin, SearchMax—the initial search window in which to search for the central ray
SearchLimitMin, SearchLimitMax—the limits of where the algorithm is allowed to search for the central ray
c(0),c(1),c(2)—initial bracket (seed points)
Cres—resolution to determine the central ray (in units of rays)
$\Delta\gamma$—angular sample pitch near the center channel
Ouput:
Cray—Central-ray value
Search Parameters:
MaxIters—maximum number of iterations to allow in search operation (suggested=30)
$\alpha_C$—bracket widening factor (use $\alpha_C$=1.5)
The initial values will preferably satisfy:
SearchLimitMin≤c(0)<c(1)<c(2)≤SearchLimitMax
The points c(0), c(1), and c(2) should be chosen somewhere near the expected cray position. The better the guesses, the less time the algorithm will take to find its answer. If the guess is poor, however, in many cases these seeds can be very different from the actual value (say 10-100 rays off) without danger of the algorithm finding the wrong value.

Generally, one will know some nominal central ray value from the scanning geometry. One may also have a reasonable guess as to the amount of typical central ray variation. Presuming these conditions, set c(1) to the nominal value, set c(0) and c(2) to the minimum and maximum typical values.

If it becomes necessary to reduce the number of input parameters, one can choose:

$$c(0) = SearchMin$$
$$c(1) = \frac{SearchMin + SearchMax}{2}$$
$$c(2) = SearchMax$$

where SearchMin and SearchMax denotes an expected range of typical central ray values. If there is no prior information about central ray, a coarse brute force search could be used to initialize the seed points.

For typical CT scans one may use Cres=0.1 but special circumstances, such as oversampling, may require finer resolution.

In this illustrative example the algorithm iteratively refines a list of three cray guesses, c(0),c(1),c(2), where the interval c(0) to c(2) is referred to as a bracket. The cray refinement is performed by evaluating MSE for each of the three points, fitting a parabola to these MSE values, finding the minimum of the parabola, and replacing one of the three c values with either the abscissa of the parabola or some nearby point outside the bracket. Once the algorithm reaches the condition where the true central ray lies between c(0) and c(2), the optimal value is said to be isolated. In typical circumstances, whenever MSE for c(1) is less than the MSE for both c(0) and c(2), the optimal value is isolated—that is, the minimum MSE is guaranteed to be somewhere inside the current bracket. Once the optimum is isolated, all future updates are performed in a way that ensures that the optimum stays isolated. The algorithm concludes successfully when the bracket is small and the optimum is isolated. A detailed description of an exemplary algorithm follows.

---

Initialize:
for i=0 to 2,
    Set e(i) = MSE(c(i),$\Delta\gamma$)
Set numiters = 0
Main Loop:
Step 1—Perform a second-order polynomial fit to data, finding the coefficients $a_0,a_1,a_2$ such that
    $e(i) = a_0 + a_1 \times (c(i) - c(1)) + a_2 \times (c(i) - c(1))^2$ for i=0,1,2
(note the polynomial is centered around c(1) in order to get good numerical stability)
The polynomial fit is performed by the following equations:

$$a_0 = e(1) \quad (23)$$

$$a_1 = \frac{(e(0) - e(1)) \times \frac{c(2) - c(1)}{c(0) - c(1)} + (e(1) - e(2)) \times \frac{c(0) - c(1)}{c(2) - c(1)}}{c(2) - c(0)} \quad (24)$$

$$a_2 = \frac{\frac{e(1) - e(0)}{c(0) - c(1)} + \frac{e(2) - e(1)}{c(2) - c(1)}}{c(2) - c(0)} \quad (25)$$

If c(0) == c(1) or c(1) == c(2), skip (24) and (25) and just set $a_2$ = 0.
Step 2—Select new search point:
If $a_2$≤0                          // parabolic fit failed to find minimum
    If e(0)<e(2),
        Set cnew = c(0) − max{Cres ,$\alpha_C$ × (c(1) − c(0))}     (26)
    Else
        Set cnew = c(2) + max{Cres ,$\alpha_C$ × (c(2) − c(1))}     (27)
Else                                       // parabolic fit found a minimum
    // set update point to abscissa for minimum of parabola $$\text{Set cnew} = c(1) - \frac{a_1}{2a_2} \quad (28)$$

```
    If cnew<c(0)
        Set cnew = max{cnew , c(0) − max{Cres,α_C × (c(1) −        (29)
            c(0))}}
    ElseIf cnew>c(2)
        Set cnew = min{cnew , c(2) + max{Cres,α_C × (c(2) −        (30)
            c(1))}}
Step 3—Evaluate MSE, update bracket
Set enew = MSE(cnew , Δγ )
If cnew < c(0)
    Set c = [cnew , c(0) , c(1)]
    Set e = [enew , e(0) , e(1)]
ElseIf enew < c(1)
    If min( e(0),enew ) ≤ min( e(1) , e(2) )
        Set c = [c(0) , cnew , c(1)]
        Set e = [e(0) , enew , e(1)]
    Else
        Set c = [cnew , c(1) , c(2)]
        Set e = [enew , e(1) , e(2)]
ElseIf cnew < c(2)
    If min( enew,e(2) ) ≤ min( e(0),e(1) ) then
        Set c = [c(1) , cnew , c(2)]
        Set e = [e(1) , enew , e(2)]
    Else
        Set c = [c(0) , c(1) , cnew]
        Set e = [e(0) , e(1) , enew]
Else
    Set c = [c(1) , c(2) , cnew]
    Set e = [e(1) , e(2) , enew]
Step 4—Check stopping conditions
If c(0) < SearchLimitMin or c(2) > SearchLimitMax
    Error condition: cannot find central ray in search window. Stop.
If c(2)−c(0) < Cres and e(1)≤e(0) and e(1)≤e(2)
    Set Cray = c(1)
    Search was successful. Stop.
numiters++
If numiters>MaxIters,
    Error condition: maximum number of iterations has been exceeded.
    Stop.
Step 5: Repeat. Go back to Step 1 of main loop
```

There are two types of failures that might be anticipated:

Detected Errors—where the algorithm cannot find the central ray and stops with an error; and Undetected Errors—where the algorithm finds an incorrect central ray but indicates success.

The following are descriptions of the possible failures. These descriptions are not needed to implement the algorithm, but may be useful when testing, debugging, or using the algorithm.

Detected errors will generally occur when:
1. There is not enough redundant data to find a match. This may be caused if chcmpmin and chcmpmax are set improperly, or if the basic scan geometry is inadequate.
2. The initial points c(0),c(1),c(2) do not provide a good starting point for the search. To correct, adjust the points to be closer to the expected cray range.
3. The search window does not include the true central ray. To correct, adjust search window to include central ray.

Undetected errors may occur when:
1. There is not enough redundant data to thoroughly refine the match. This may be caused if the basic scan geometry is inadequate. Increasing MinOverlap will help to detect these types of errors. Adjusting chcmpmin and chcmpmax may also help. If parameters are reasonably set this should only be a danger for asymmetric scanning or for acquisitions a good bit less than 360°.
2. The initial bracket was too large and included multiple optima. Shrink the initial bracket. If this happens the central ray will likely be off by many tens or hundreds of rays and should be very obvious in the reconstruction.

In general one wishes for such an algorithm to:
1. Find the cray to a fine resolution;
2. Allow lots of slop when picking seed values; and
3. Find the cray in a short amount of time.

Unfortunately, in general one will usually only be able to improve one of these three at the expense of another. The time required for the algorithm will be closely proportional to the number of MSE evaluations that are carried out. The algorithm described requires 3 initial evaluations, plus 1 evaluation per iteration. If none of the initial points are within Cres of the true central ray, the algorithm will require a minimum of 6 evaluations.

It will be recalled that both the central ray and the sample spacing can be used in conjunction with these teachings. In the detailed description provided above, Δγ was an input. By one approach, however, this value can comprise an output. That is, one can jointly find both central ray and Δγ by finding the values of cray and Δγ that minimize MSE(cray,Δγ). Note that finding the sample spacing Δγ is equivalent to finding the fan angle FA since for an equi-angular detector:

$$FA=(N_{ch}-1)\Delta\gamma \quad (31)$$

and for an equi-spatial detector, $$FA=\tan^{-1}((Nch-1-cray)\times\Delta\gamma)+\tan^{-1}(cray\times\Delta\gamma) \quad (32)$$

As before, one could use an off-the shelf algorithm to perform the minimization, but the algorithm must now be suited to a 2 dimensional search. A newer approach will now be described:

Input:
  CSearchMin, CsearchMax—the initial interval in which to search for the central ray
  FSearchMin, FsearchMax—the initial interval in which to search for Δγ
  CSearchLimitMin, CsearchLimitMax—the interval in which the algorithm is allowed to search for the central ray
  FSearchLimitMin, FsearchLimitMax—the interval in which the algorithm is allowed to search for Δγ
  c(0),c(1),c(2)—initial cray sample points
  f(0),f(1),f(2)—initial Δγ sample points
  Cres—resolution to determine the central ray (in units of rays)
  Fres—resolution to determine Δγ
  Search Parameters:
  MaxIters—maximum number of iterations to allow in search operation (recommend 50)
  $\alpha_C$, $\alpha_F$—bracket widening factors (set both=1.5)
Output:
  Cray—central ray
  Δγ—angular sample spacing at the center channel By one approach the initial values should satisfy:
  CSearchLimitMin≤c(0)<c(1)<c(2)≤CSearchLimitMax
  FSearchLimitMin≤f(0)<f(1)<f(2)≤FSearchLimitMax The C and F search ranges should encompass the true central ray and the true Δγ, respectively. The seed values c and f can be initialized directly using 3 seed points, or by using initial search windows, $$c(0) = C\text{search}\text{Min}$$

$$c(1) = \frac{C\text{search}\text{Min} + C\text{search}\text{Max}}{2}$$

$$c(2) = C\text{search}\text{Max}$$

$$f(0) = F\text{search}\text{Min}$$

-continued
$$f(1) = \frac{F\text{search}\text{Min} + F\text{search}\text{Max}}{2}$$

$$f(2) = F\text{search}\text{Max}$$

For successful convergence, this algorithm tends to require a much smaller initial c bracket than the cray only search does. The initial bracket should generally be at most about 5 rays wide. Experience shows that if the cray is not adequately refined before searching for sample spacing, then the sample spacing calibration is likely to fail with error. If the central ray is not approximately known ahead of time, run the 1D Cray-Only search first using a coarse resolution (for example Cres=5) and the nominal $\Delta\gamma$, then use the final bracket as the initial c bracket for this algorithm.

An illustrative two dimensional search algorithm is as follows:

Initialize:
  for i=0 to 2,
    for j=0 to 2,
      set e(i,j)=MSE(c(i),f(j))
numiters=0
Main Loop:
Step 1—Perform a second-order 2D polynomial fit to data, finding the coefficients $a_0, \ldots, a_5$ such that:

$$e(i, j) = \qquad (33)$$
$$a_o + a_1 \times (c(i) - c(1)) + a_2 \times (f(j) - f(1)) + a_3 \times (c(i) - c(1))^2 +$$
$$a_4 \times (f(j) - f(1))^2 + a_5 \times (c(i) - c(1)) \times (f(j) - f(1))$$

for i=0,1,2 and j=0,1,2

(note the polynomial is centered around (c(1),f(1)) in order to get good numerical stability). The polynomial fit may be performed by off-the-shelf tools. One prior art approach (see "Numerical Recipes in C: The Art of Scientific Computing" by Press et al.), for example, gives a method for minimizing $$\sum_{i=0}^{N-1} \left[ y_i - \sum_{k=0}^{M-1} a_k X_{k,i} \right]^2$$

This method can be used here by letting N=9 and M=6 and using $$y = [e(0, 0), e(0, 1), e(0, 2), e(1, 0), e(1, 1), e(1, 2), e(2, 0), e(2, 1), e(2, 2)]$$

$$X = \begin{bmatrix}
1 & (c(0)-c(1)) & (f(0)-f(1)) & (c(0)-c(1))^2 & (f(0)-f(1))^2 & (c(0)-c(1)) \times (f(0)-f(1)) \\
1 & (c(0)-c(1)) & 0 & (c(0)-c(1))^2 & 0 & 0 \\
1 & (c(0)-c(1)) & (f(2)-f(1)) & (c(0)-c(1))^2 & (f(2)-f(1))^2 & (c(0)-c(1)) \times (f(2)-f(1)) \\
1 & 0 & (f(0)-f(1)) & 0 & (f(0)-f(1))^2 & 0 \\
1 & 0 & 0 & 0 & 0 & 0 \\
1 & 0 & (f(2)-f(1)) & 0 & (f(2)-f(1))^2 & 0 \\
1 & (c(2)-c(1)) & (f(0)-f(1)) & (c(2)-c(1))^2 & (f(0)-f(1))^2 & (c(2)-c(1)) \times (f(0)-f(1)) \\
1 & (c(2)-c(1)) & 0 & (c(2)-c(1))^2 & 0 & 0 \\
1 & (c(2)-c(1)) & (f(2)-f(1)) & (c(2)-c(1))^2 & (f(2)-f(1))^2 & (c(2)-c(1)) \times (f(2)-f(1))
\end{bmatrix}$$

One can also find the polynomial coefficients through the matrix operations, $$a = (X^T X)^{-1} X^T y$$

The choice of fitting method is left up to the implementer.

---

Step 2—Select new Cray search point:
If $a_3 \leq 0$      // parabolic fit failed to find minimum
  If e(0,1)<e(2,1), set cnew = c(0) − max{Cres ,$\alpha_C \times$ (c(1) −    (34)
  c(0)))}
  Else set cnew = c(2) + max{Cres ,$\alpha_C \times$ (c(2) − c(1)))}    (35)
Else      // parabolic fit found a minimum
  If $a_5$ == 0, (or $a_5$ is small compared to floating point accuracy)

$$\text{Set cnew} = c(1) - \frac{a_1}{2a_3} \qquad \text{// minimum of 1D parabola} \qquad (36)$$

Else $$\text{cnew} = c(1) + \frac{2a_1 a_4 - a_2 a_5}{a_5^2 - 4a_3 a_4} \qquad \text{// minimum of 2D parabola} \qquad (37)$$

If cnew<c(0)
    Set cnew = max{cnew , c(0) − max{Cres,$\alpha_C \times$ (c(1) −    (38)
    c(0))}}
  ElseIf cnew>c(2)
    Set cnew = min{cnew , c(2) + max{Cres,$\alpha_C \times$ (c(2) −    (39)
    c(1))}}
Step 3, Select new $\Delta\gamma$ search point:
If $a_4 \leq 0$      // parabolic fit failed to find minimum
  If e(1,0)<e(1,2), set fnew = f(0) − max{Fres ,$\alpha_F \times$ (f(1) −    (40)
  f(0)))}
  Else set fnew = f(2) + max{Fres ,$\alpha_F \times$ (f(2) − f(1)))}    (41)
Else      // parabolic fit found a minimum
  If $a_5$ == 0, (or small compared to floating point accuracy)    (42)

$$\text{Set fnew} = f(1) - \frac{a_2}{2a_4} \qquad \text{// minimum of 1D parabola}$$

Else $$\text{fnew} = f(1) + \frac{2a_2 a_3 - a_1 a_5}{a_5^2 - 4a_3 a_4} \qquad \text{// minimum of 2D parabola} \qquad (43)$$

If fnew<f(0)
    Set fnew = max{fnew , f(0) − max{Fres,$\alpha_F \times$ (f(1) −    (44)
    f(0))}}
  ElseIf fnew>f(2)
    Set fnew = min{fnew , f(2) + max{Fres,$\alpha_F \times$ (f(2) −    (45)
    f(1))}}
Step 4—Evaluate MSE, update brackets
Set enew = MSE( cnew, fnew)
If cnew<c(0)
  Set clist = [ "new" 0 1]

-continued

```
ElseIf cnew < c(1)
    Find the minimum of { e(0,1) , e(1,1) , e(2,1) , enew }
    If min is e(0,1) or enew,
        Set clist = [0 "new" 1]
    Else
        Set clist = ["new" 1 2]
ElseIf cnew < c(2)
    Find the minimum of { e(0,1) , e(1,1) , e(2,1) , enew }
    If min is e(0,1) or e(1,1),
        Set clist = [0 1 "new"]
    Else
        Set clist = [1 "new" 2]
Else
        Set clist = [1 2 "new"]
If fnew<f(0)
    Set flist = [ "new" 0 1]
ElseIf fnew < f(1)
    Find the minimum of { e(1,0) , e(1,1) , e(1,2) , enew }
    If min is f(0,1) or enew,
        Set flist = [0 "new" 1]
    Else
        Set flist = [ "new" 1 2]
ElseIf fnew < f(2)
    Find the minimum of { e(1,0) , e(1,1) , e(1,2) , enew }
    If min is e(0,1) or e(1,1),
        Set flist = [0 1 "new"]
    Else
        Set flist = [1 "new" 2]
Else
    Set flist = [1 2 "new"]
For i=0 to 2,
    If clist(i)="new"
        c_next(i) = cnew
    else
        c_next (i) = c( clist(i) )
For j=0 to 2,
    If flist(j)="new"
        f_next(j) = fnew
    else
        f_next(j) = f( clist(j) )
For i=0 to 2,
    For j=0 to 2,
        If clist(i)="new" and flist(i)="new"
            e_next (i,j) = enew
        Elseif clist(i) = "new"
            e_next (i,j) = MSE( cnew, f( flist(j) ) )
        Elseif flist(j) = "new"
            e_next (i,j) = MSE( c( clist (i) ) , fnew )
        Else
            e_next (i,j) = e( clist(i) , flist(j) )
Set e = e_next
Set c = c_next
Set f = f_next
Step 5—Check stopping conditions
If (c(0) < CSearchLimitMin) or (c(2) > CSearchLimitMax ) or (f(0) <
FSearchLimitMin) or (f(2) > FSearchLimitMax ),
    Error condition: cannot find optimum inside search window. Stop.
If (c(2) – c(0) < Cresolution) and ( f(2) – f(0) < Fresolution ) and
min e(i, j) == e(1,1)
  i,j
    Set cray = c(1)
    Set Δγ = f(1)
    Search was successful. Stop.
numiters++
If numiters>MaxIters,
    Error condition: maximum number of iterations has been exceeded.
    Stop.
Step 6—Repeat. Go back to beginning of main loop
```

Those skilled in the art will appreciate that these teachings present a variety of ways to greatly reduce or to eliminate dedicated calibration scans and/or the use of calibration objects with computed tomography equipment. The scanning data itself for a given scanned object of interest contains information that, when properly leveraged by these teachings, allows a kind of self-calibration to occur. As a result, efficiency and productivity may be improved without detriment to the veracity and accuracy of the final projection results. It will also be recognized and appreciated by those skilled in the art that these teachings may be applied for alignment purposes. For example, one may want to position the central ray at a specific location. This might be desirable, for example, when a particular detector channel is known to be the best detector channel and one wishes to place the central ray in alignment with that particular detector channel. These teachings are readily applied to permit knowing where the central ray is so that one then knows which way to arrange things in order to achieve such alignment.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

I claim:

1. A method comprising:
providing an energy source and a corresponding detector array comprising multiple detector channels;
providing an object;
causing relative movement of at least one of the energy source and the corresponding detector array with respect to the object about an axis of rotation;
using the energy source and the corresponding detector array while causing the relative movement to scan the object to obtain object projection data;
using the object projection data for a plurality of the multiple detector channels to determine a parameter as corresponds to at least one scanning geometry characteristic as corresponds to using the energy source and the corresponding detector array while causing the relative movement to scan the object, such that the parameter is determined even when the object comprises an object other than a calibration object and is being projected to facilitate a study of the object other than solely as part of calibrating usage of the energy source and the corresponding detector array, wherein the scanning geometry characteristics comprises a value that corresponds to a sample pitch.

2. The method of claim 1 wherein the energy source comprises an X-ray energy source.

3. The method of claim 1 wherein causing relative movement of at least one of the energy source and the corresponding detector array with respect to the object about an axis of rotation further comprises holding the object using a support structure.

4. The method of claim 3 wherein causing relative movement of at least one of the energy source and the corresponding detector array with respect to the object about an axis of rotation further comprises causing the support structure to rotate about the axis of rotation.

5. The method of claim 3 wherein causing relative movement of at least one of the energy source and the corresponding detector array with respect to the object about an axis of rotation further comprises causing at least the energy source to rotate about the axis of rotation.

6. The method of claim 5 wherein causing relative movement of at least one of the energy source and the corresponding detector array with respect to the object about an axis of rotation further comprises causing the corresponding detector array to rotate about the axis of rotation.

7. The method of claim 1 wherein using the object projection data to determine a parameter comprises using logarithmic values of the object projection data to determine the parameter.

8. The method of claim 1 further comprising:
using the parameter when processing the object projection data to provide corrected objected projection data.

9. A method comprising:
providing an energy source and a corresponding detector array comprising multiple detector channels;
providing an object;
causing relative movement of at least one of the energy source and the corresponding detector array with respect to the object about an axis of rotation;
using the energy source and the corresponding detector array while causing the relative movement to scan the object to obtain object projection data;
using the object projection data for a plurality of multiple detector channels to determine a parameter as corresponds to at least one scanning geometry characteristic as corresponds to using the energy source and the corresponding detector array while causing the relative movement to scan the object, such that the parameter is determined even when the object comprises an object other than a calibration object and is being projected to facilitate a study of the object other than solely as part of calibrating usage of the energy source and the corresponding detector array, wherein using the object projection data to determine a parameter as corresponds to at least one scanning geometry characteristic comprises:
processing the object projection data to provide a first set of projection data formed using a set of data points;
using a selected value for the parameter and data comprising complements to the set of data points to provide a second set of projection data;
comparing the first set of projection data to the second set of projection data to determine a measure of similarity.

10. The method of claim 9 wherein using the object projection data to determine a parameter as corresponds to at least one scanning geometry characteristic further comprises:
assessing the measure of similarity;
using the selected value as a parameter to describe the scanning geometry characteristic as a function of assessing the measure of similarity.

11. The method of claim 10 wherein using the object projection data to determine a parameter as corresponds to at least one scanning geometry characteristic further comprises:
selecting a new value for the parameter that is different than the selected value for the parameter and using the new value for the parameter as the selected value for the parameter while repeating the above steps beginning with using a selected value for the parameter and processing the object projection data as a function of assessing the measure of similarity.

12. The method of claim 9 wherein using a selected value for the parameter comprises:
providing a plurality of candidate parameter values;
selecting one of the plurality of candidate parameter values to use as the selected value.

13. The method of claim 12 wherein providing a plurality of candidate parameter values comprises providing three candidate parameter values.

14. The method of claim 12 wherein using the object projection data to determine a parameter as corresponds to at least one scanning geometry characteristic further comprises:
assessing the measure of similarity;
selecting a new value for the parameter that is different than the selected value for the parameter, as a function of assessing the measure of similarity, by:
deleting a selected one of the plurality of candidate parameter values;
adding a new candidate parameter value to the plurality of candidate parameter values to provide a new plurality of candidate parameter values;
selecting one of the plurality of candidate parameter values to use as the selected value when redoing at least some of the foregoing steps.

15. The method of claim 9 wherein comparing the first set of projection data to the second set of projection data to determine a measure of similarity comprises at least one of the following:
determining a squared error as corresponds to differences between the first set of projection data and the second set of projection data;
determining mutual information between the first set of projection data and the second set of projection data;
determining a correlation between the first set of projection data and the second set of projection data.

* * * * *

UNITED STATES PATENT AND TRADEMARK OFFICE
CERTIFICATE OF CORRECTION

| | | |
|---|---|---|
| PATENT NO. | : 9,052,265 B2 | Page 1 of 1 |
| APPLICATION NO. | : 11/419793 | |
| DATED | : June 9, 2015 | |
| INVENTOR(S) | : Kevin Holt | |

It is certified that error appears in the above-identified patent and that said Letters Patent is hereby corrected as shown below:

IN THE CLAIMS:

Claim 1, Column 18, Line 44; delete "characteristics" and insert --characteristic--.
Claim 1, Column 18, Line 44; delete "to a" and insert --to--.
Claim 8, Column 19, Line 7; delete "objected" and insert --object--.

Signed and Sealed this
Third Day of November, 2015

Michelle K. Lee
*Director of the United States Patent and Trademark Office*